(12) United States Patent
Sarma et al.

(10) Patent No.: US 11,445,972 B2
(45) Date of Patent: Sep. 20, 2022

(54) BRAIN-COMPUTER INTERFACE FOR USER'S VISUAL FOCUS DETECTION

(71) Applicant: Massachusetts Institute of Technology, Cambridge, MA (US)

(72) Inventors: Sanjay E. Sarma, Belmont, MA (US); Alex Armengol Urpi, Sant Sadurni d'Anoia (ES)

(73) Assignee: Massachusetts Institute of Technology, Cambridge, MA (US)

( * ) Notice: Subject to any disclaimer, the term of this patent is extended or adjusted under 35 U.S.C. 154(b) by 712 days.

(21) Appl. No.: 16/379,096

(22) Filed: Apr. 9, 2019

(65) Prior Publication Data

US 2019/0307356 A1 Oct. 10, 2019

Related U.S. Application Data

(60) Provisional application No. 62/655,106, filed on Apr. 9, 2018.

(51) Int. Cl.
*A61B 5/378* (2021.01)
*A61B 5/00* (2006.01)
*A61B 5/16* (2006.01)

(52) U.S. Cl.
CPC .............. *A61B 5/378* (2021.01); *A61B 5/161* (2013.01); *A61B 5/6803* (2013.01); *A61B 5/7282* (2013.01)

(58) Field of Classification Search
CPC ....... A61B 5/161; A61B 5/378; A61B 5/6803; A61B 5/7282; G06F 3/011; G06F 3/015
See application file for complete search history.

(56) References Cited

U.S. PATENT DOCUMENTS

2014/0058483 A1\* 2/2014 Zao ........................ A61B 5/378
607/88
2017/0035317 A1 2/2017 Jung et al.

FOREIGN PATENT DOCUMENTS

WO WO-2012037610 A1 \* 3/2012 ........... A61B 5/7282

OTHER PUBLICATIONS

Armengol Urpi, Alexandre, et al. "Brainwave-Augmented Eye Tracker: High-Frequency SSVEPs Improves Camera-Based Eye Tracking Accuracy" Mar. 22-25, 2022. 27th International Conference on Intelligent User Interfaces. (Year: 2022).\*

(Continued)

*Primary Examiner* — Christian Jang
*Assistant Examiner* — Anna Roberts
(74) *Attorney, Agent, or Firm* — Wolf, Greenfield & Sacks, P.C.

(57) ABSTRACT

According to various aspects, a new concept of Steady-State Visually Evoked Potential (SSVEP) based Brain-Computer Interface (BCI) is described where brain-computer communication occurs by capturing SSVEP induced by consciously imperceptible visual stimuli integrated into, for example, a virtual scene. These consciously imperceptible visual stimuli are able to convey subliminal information to a computer. In various embodiments, computer based operations can be mapped to visual elements with associated flickering stimuli, and induced SSVEP can be detected when the user focused upon them. In various embodiments, these visual elements can be introduced into existing display without any perceivable change to content being displayed.

20 Claims, 9 Drawing Sheets

(56) References Cited

OTHER PUBLICATIONS

Armengol Urpi, Alexandre and Sanjay E. Sarma. "Sublime: a handsfree virtual reality menu navigation system using a high-frequency SSVEP-based brain-computer interface." Nov. 2018, Proceedings of the ACM Symposium on Virtual Reality Software and Technology (Year: 2018).*

International Search Report and Written Opinion dated Jul. 5, 2019 in connection with International Application No. PCT/US2019/026516.

* cited by examiner

BRAIN-COMPUTER INTERFACE FOR USER'S VISUAL FOCUS DETECTION

RELATED APPLICATIONS

This Application claims the benefit under 35 U.S.C. § 119(e) to U.S. Provisional Application Ser. No. 62/655,106, entitled "BRAIN-COMPUTER INTERFACE FOR USER'S VISUAL FOCUS DETECTION" filed on Apr. 9, 2018, which is herein incorporated by reference in its entirety.

BACKGROUND

Steady-state visually evoked potentials (SSVEP) are brain signals generated at the visual cortex, which occur in response to visual stimulation at specific frequencies. When the retina is excited with flickering stimuli at a particular frequency within the 6-90 Hz range, electrical potentials at the same frequency and harmonics are generated in the occipital area of the brain. Various conventional approaches have discussed using this phenomenon to build brain-computer interfaces (BCIs). In conventional implementations, these BCIs use visual stimuli rendered in computer screens or with light sources modulated at a specified frequency to elicit response signals at the visual cortex. The response signals can be captured by electroencephalogram ("EEG") equipment and processed to identify which stimulus the subject is looking at. Using SSVEPs, BCIs have been implemented to capture a variety of actions including spelling words, controlling a robot, or playing video games.

As for the stimulating frequencies used, it has been widely proved that the brain does not respond uniformly throughout all the spectrum, i.e. it resonates more strongly to some frequencies than others, giving the highest SSVEP amplitudes (easiest to detect) in the 6-16 Hz band.

SUMMARY

The inventors have discovered that at high enough frequencies optical perception can no longer distinguish that a visual element is flickering (e.g., >40 Hz), and that these visual elements with associated flickering stimuli can be integrated into various display without perceptible impact on the displayed content. Although conscious perception cannot identify the flickering stimuli above certain frequencies, the brain and respective visually evoked potentials are still correlated to the visual element, and its associated flickering frequency (and/or a respective pattern/harmonics executed by the visual element). Thus, various embodiments can detect what visual element in a content display the user is focusing on, without any perceptible change detectable by the system user. These "invisible" stimuli link user visual focus to executable operations and do so without the drawbacks of various conventional systems.

According to various aspects, the inventor have developed a brain-computer interface having a stimuli generator for creating flickering stimuli having associated flicker rates at imperceptible frequencies, a detection component to identify evoked potentials in user's brain activity, and an execution component that selects computer operations to trigger responsive to identification of the evoked potentials associated with respective visual elements (e.g., and their flicker rate, harmonics, or flicker pattern, among other options.)

In further aspects, some conventional implementations have used SSVEP-based BCI within virtual environments, however, these conventional applications superimpose basic shapes (e.g., squares or circles) to present the flickering stimuli. The inventors have realized that these conventional approaches detract and obscure the display and can result in a less immersive experience for the user. Other conventional approaches have attempted to resolve this issue by integrating stimuli directly into the existing visual environment. However, these approaches still obscure or detract from the graphical display based on use of stimulating frequencies in the low (1-12 Hz) or medium (12-25 Hz) part of the spectrum. The inventors have realized that such implementation presents major disadvantages: including at least, low frequency flickering lights (5-25 Hz) are annoying and cause visual fatigue to the user, and flashing stimuli, especially in the 15-25 Hz range, have the potential to induce photo-epileptic seizures.

Accordingly, various aspects discussed resolve some of the issues present in low frequency SSVEP and/or issues present in superimposing shapes into visual displays. According to various embodiments, at least some of the issues with conventional approaches are avoided using a high-frequency band (>40 Hz) stimuli. In further aspects, the flickering stimuli is generated at frequencies fast enough that visual perception cannot detect the flicker. The rate beyond which flickering cannot be consciously perceived is referred to as the critical fusion rate. In some embodiments this can be set to occur at frequencies above 40 Hz. Using flickering stimuli that are not consciously perceived enables various embodiments to create a subtle yet powerful feature set and that establishes a subconscious connection between user and computer grounded in "undetectable" visual stimuli (i.e., stimuli that the user is not consciously aware of).

In further aspects, using higher range frequencies, various interfaces are able to produce stimuli in respective displays that are not consciously perceptible, but still create detectable and usable SSVEP in the brain. According to various aspects, this represents a significant improvement in user interface design by eliminating bulky and distracting visual stimuli that generally obscure the display into which they are integrated. In interface design, this also enables introduction of visual stimuli elements without the conventional detriment to the displayed graphics. In broad summary, the visual elements are perceptibly invisible to the user but trigger detectable potentials for interactive functionality.

According to another embodiment, because the stimuli are not consciously perceivable, they can be integrated seamlessly into any existing content without any apparent change to the displayed content. According to further embodiments, the system enables implementation of far more visual stimuli without distraction or detriment to the display. Displaying more visual elements with associated stimuli frequencies and/or patterns within the display increases the resolution/functionality of the interface itself and does so without detracting from the display in which the stimuli are integrated. In the context of any interactive display (e.g., gaming, learning, etc.), this enables richer and more detailed visualizations and enables embedding and/or triggering of more operations without adverse effect on the displays themselves.

According to one aspect, a system for controlling a brain computer interface is provided. The system comprises at least one processor operatively connected to a memory, a stimulus generator, executed by the at least one processor, configured to generate visual elements for rendering in a display without perceptible effect on the display, the visual element having an associated flicker rate executed at a frequency exceeding a critical fusion rate, at least one electroencephalogram (EEG) sensor to capture brain activity of a user observing a display including at least one visual element, and wherein the at least one processor is configured to: detect a visually evoked potential in the captured brain activity associated with the at least one visual element; and trigger at least one computer function mapped to the respective visual element.

According to one aspect a system for controlling a brain computer interface is provided. The system comprises at least one processor operatively connected to a memory; a stimulus generator, executed by the at least one processor, configured to generate visual elements for rendering in a display of content without perceptible effect on the display of content, the visual element having an associated flicker rate executed at a frequency exceeding a critical fusion rate; at least one electroencephalogram (EEG) sensor to capture brain activity of a user observing a display including at least one visual element; and wherein the at least one processor is configured to: detect a visually evoked potential in the captured brain activity associated with the at least one visual element; and trigger at least one computer function mapped to the respective at least one visual element.

According to one embodiment, the stimulus generator is configured to modify an existing display of content to incorporate the visual elements. According to one embodiment, the stimulus generator is configured to modify the existing display without perceptible change to a viewing user relative to the unmodified display. According to one embodiment, the at least one processor is configured to generate the visual elements with amplitude reduction of the stimulus signal relative to a maximum/minimum stimulation pattern. According to one embodiment, respective visual elements concurrently observable in a display are associated with respective unique signaling properties.

According to one embodiment, the respective visual elements are associated with respective unique SSVEP based on associated unique signaling properties. According to one embodiment, the at least one processor is configured to identify a presence of the unique SSVEP in the captured brain activity from the at least one EEG sensor. According to one embodiment, the stimulus generator is configured to generate the plurality of visual elements with the respective unique signaling properties, and wherein the respective unique signaling properties include at least one of unique frequency, unique stimulation pattern, unique stimulation timing, and unique stimulation encoding.

According to one embodiment, the at least one processor is further configured to process time intervals of EEG data at partially overlapping time periods.

According to one aspect, a method for controlling a brain computer interface is provided. The method comprises generating, by at least one processor, visual elements for rendering in a display of content, wherein generating the visual elements includes generating at least one visual element having an associated flicker rate at a frequency exceeding a critical fusion rate; capturing, by the at least one processor, brain activity of a user observing a display including the at least one visual element from at least one electroencephalogram (EEG) sensor; detecting, by the at least one processor, a visually evoked potential in the captured brain activity associated with the at least one visual element; and triggering, by the at least one processor, at least one computer function mapped to the respective visual element.

According to one embodiment, the method further comprises an act of modifying, by the at least one processor an existing display of content to incorporate the visual elements. According to one embodiment, the act of modifying the existing display is executed without perceptible change to a viewing user relative to the unmodified display. According to one embodiment, the method further comprises generating, by the at least one processor, the visual elements with amplitude reduction in an associated flickering stimulus signal relative to a maximum/minimum stimulation pattern. According to one embodiment, the method further comprises associating, by that at least one processor, respective visual elements concurrently observable in a display with respective unique signaling properties.

According to one embodiment, the method further comprises associating, by that at least one processor, the respective visual elements are associated with respective unique SSVEP based on associated unique signaling properties. According to one embodiment, the method further comprises, identifying, by the at least one processor, a presence of the unique SSVEP in the capture brain activity from the at least one EEG sensor. According to one embodiment, the act of generating the plurality of visual elements with the respective unique signaling properties includes an act of generating respective visual elements with at least one of: a unique frequency, a unique stimulation pattern, a unique stimulation timing, and a unique stimulation encoding. According to one embodiment, the at least one processor is further configured to process time intervals of EEG data at partially overlapping time periods.

According to one aspect, a computer-readable medium having computer readable instructions when executed cause a computer to execute a method for controlling a brain computer interface is provided. The method comprises generating visual elements for rendering in a display of content, wherein generating the visual elements includes generating at least one visual element having an associated flicker rate at a frequency exceeding a critical fusion rate; capturing brain activity of a user observing a display including the at least one visual element from at least one electroencephalogram (EEG) sensor; detecting a visually evoked potential in the captured brain activity associated with the at least one visual element; and triggering at least one computer function mapped to the respective visual element.

According to one embodiment, the method further comprises an act of modifying, by the at least one processor an existing display of content to incorporate the visual elements without perceptible change to a viewing user relative to the unmodified display.

Still other aspects, examples, and advantages of these exemplary aspects and examples, are discussed in detail below. Moreover, it is to be understood that both the foregoing information and the following detailed description are merely illustrative examples of various aspects and examples, and are intended to provide an overview or framework for understanding the nature and character of the claimed aspects and examples. Any example disclosed herein may be combined with any other example in any manner consistent with at least one of the objects, aims, and needs disclosed herein, and references to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DETAILED DESCRIPTION

The inventors have discovered that at high enough frequencies optical perception can no longer distinguish that a visual element is flickering (e.g., >40 Hz), and that these visual elements with associated flickering stimuli can be integrated into various displays without perceptible impact on the displayed content. Although conscious perception cannot identify the flickering stimuli, the brain and respective visually evoked potentials are still correlated to the visual element, and its associated flickering frequency (and/or a respective pattern/harmonics executed by the visual element). Thus, various embodiments can detect what visual element in a content display the user is focusing on, without any perceptible change that is consciously detectable by the system user. These "invisible" stimuli link user focus to executable operations and do so without the drawback of various conventional systems. According to various aspects, the inventors have developed a brain-computer interface having a stimuli generator for creating flickering stimuli and associated flicker rates at imperceptible frequencies, a detection component configured to identify evoked potentials in the user's brain activity, and an execution component that selects computer operations to trigger responsive to identification of the evoked potentials associated with the respective visual elements (e.g., via their flicker rate, harmonics, or flicker pattern, among other options.)

In further aspects, a new concept of Steady-State Visually Evoked Potential (SSVEP) based Brain-Computer Interface (BCI) is described where brain-computer communication occurs by capturing SSVEP induced by consciously imperceptible visual stimuli integrated into, for example, a virtual scene. These consciously imperceptible visual stimuli are able to convey subliminal information to a computer. Various embodiments were tested in a virtual reality (VR) environment, where the subject was able to navigate between different menu displays by just gazing at them, and each menu display included different SSVEP stimuli without the user being aware of the presence of these new visual elements having associated flickering stimuli.

Figure 1:
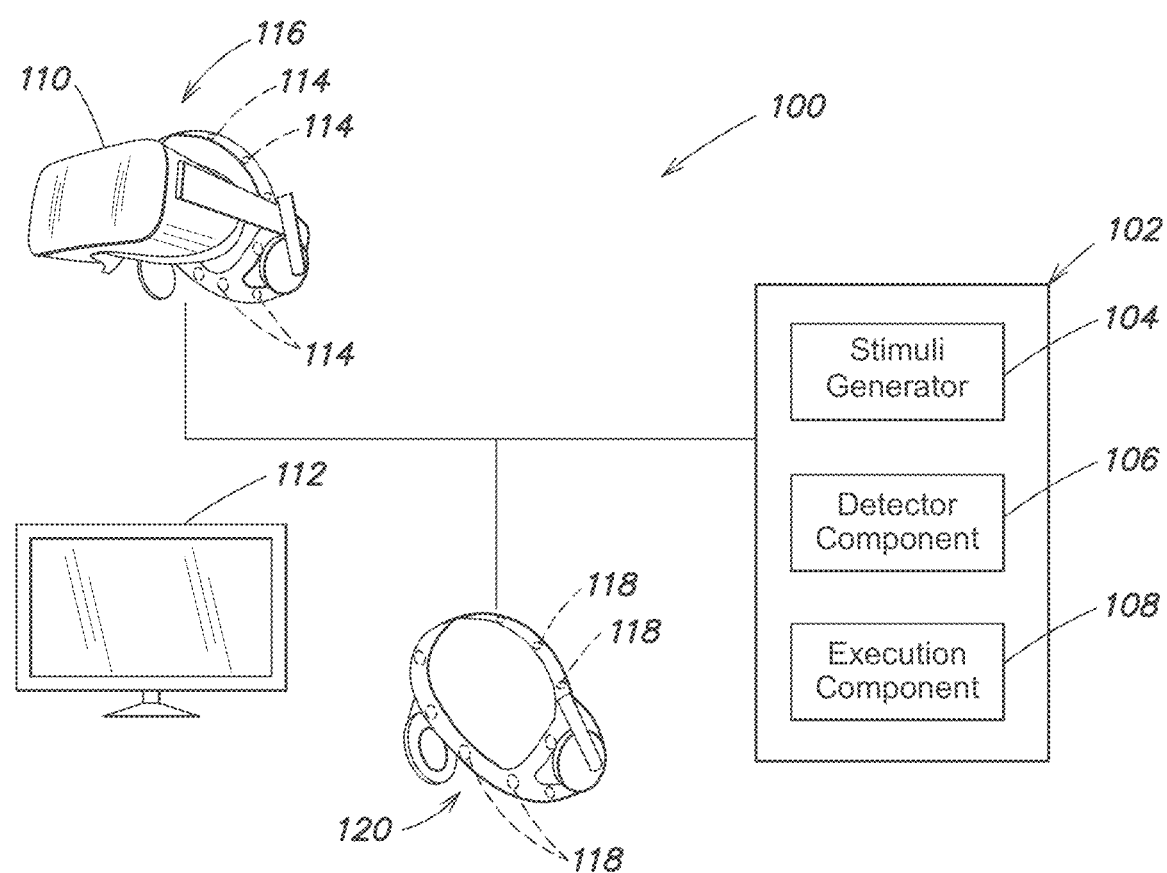
FIG. 1 is a block diagram of an example system for controlling a brain computer interface, according to one embodiment.

FIG. 1 is a block diagram of an example system 100 for managing a brain computer interface that operates imperceptibly to a user's conscious awareness. According to various embodiments, system 100 can be instantiated to execute the various functions and/or algorithms discussed herein. In some embodiments, the system 100 can include an interface engine 102 configured to execute the discussed functions, algorithms, etc., and/or to instantiate specialized components configured to manage specific functions, algorithms, and/or operations discussed in greater detail below.

Stated broadly, various embodiments of system 100 generate flashing stimuli having flashing frequencies faster than the critical fusion rate for conscious perception. As discussed above, at high enough frequencies optical perception can no longer distinguish that a visual element is flickering (e.g., >40 Hz). Although conscious perception cannot identify the flickering stimuli, the brain and respective visually evoked potentials are still correlated to the visual element, and its associated flickering frequency (and/or a respective pattern/harmonics executed by the visual element). Thus, system 100 can integrate visual elements that have no apparent visual effect on a display (e.g., 110 or 112) but can be detected from data captured by EEG sensors. According to one embodiment, these visual elements are integrated seamlessly into a display—thus there is no perceptible awareness by a user that a visual element and associated flicker is in the display at all. Stimuli operating above the critical fusion rate and that are provided without obscuring a visual display produce significantly improved display environments over conventional approaches.

According to one embodiment, system 100 and/or engine 102 can include a stimuli generator 104 configured to generate one or more visual elements that can be integrated into an existing display or built into a new display. According to various embodiments, the stimuli generator 104 can be configured to modify elements of an existing display to flicker at frequencies above the critical fusion rate. In further embodiments, the visual elements (e.g., new or modified existing visual elements) can have flickering patterns or harmonics specified by the stimuli generator. Various signal generation/detection approaches can be implemented by the stimuli component (e.g., analogous to time-division multiple access (TDMA), frequency division multiple access (FDMA), code-division multiple access (CDMA), etc.) using differing frequencies, pattern and/or harmonics, with the underlying signaling occurring at least at the critical fusion frequency. In further embodiments, various other signaling approaches can be used to produce stimuli and correlate EEG data to the respective stimuli (including for example, analogous to 4G, LTE, and/or 5G, among other options and various combinations of signaling options).

According to some embodiments, EEG sensors (e.g., 114) are embedded in a virtual reality display/headset (e.g., 116). In various alternatives, a standard display screen (e.g., 112) can also be used in conjunction with EEG sensors (e.g., 118) and a headset (120). SSVEP evoked by visual elements in such displays can be captured by the sensors and specific signals associated with respective visual elements detected, for example, by the system 100 and/or engine 102. According to some embodiments, the system 100 and/or engine 102 can instantiate a detector component 106 configured to analyze data captured by the EEG or equivalent sensors. Analysis of the EEG data enables the system 100, engine and/or detector component 106 to determine which visual elements a user is focusing on in the display. Based on the flickering frequency, pattern, and/or harmonics associated with a respective visual element, the associated SSVEP can be identified from the EEG data. In a naïve example, a visual element having a flicker rate at 40 Hz can be shown in one portion of a display and another having a flicker rate at 60 Hz can be shown in another, as data is collected and analyzed it can be determined which visual element is being viewed.

According to further embodiments, each visual element shown in a display can trigger an associated action. According to one embodiment, the system 100 and/or engine can include an execution component 108 configured to generate, access and/or execute mappings between visual elements and respective computer functions. Returning to the naïve example, a visual element displayed on a right side of the display can be associated with an animation that displays movement towards the right side of the screen, which in turn can bring new visual elements into the newly rendered portions of the display, each having associated computer functions. In further embodiments, the system 100 can also be configured to operate as an interface layer configured to manage/detect input selections (e.g., interpreting what object is being looked at as a selection) and translate those inputs into input selections recognized by an underlying program (e.g., map the object being looked at to a mouse click or touch input, among other options). In various embodiments, the system can function as a visual interface augmentation layer or as an application programming interface (API) configured to accept and process visual selections (e.g., viewing an object) and map detected visual selections to native input operations (e.g., mouse click) already established as part of respective programs.

Example Implementation

According to one embodiment, a BCI system can include a VR headset augmented with EEG sensors that permit capture of visually evoked potentials from captured brain signals. Further, the BSI system implements a novel concept in SSVEP-based BCI that allows the user to unconsciously communicate subliminal information to the computer based on the displays presented to the user (e.g., in a virtual environment). Broadly stated, various implementations provide:

(1) visual stimuli frequencies that exceed a flicker fusion rate, i.e., the frequency at which a flashing light appears to be steady to a human eye (as the human eye cannot perceive that a light is flashing above a certain frequency, the flashing frequency is invisible or not consciously perceptible to the user); and (2) visual elements having flickering stimuli integrated into objects already present in a display—for example, by flickering virtual objects shown in a virtual environment rather than inserting fiducials (e.g. rectangles or circles, etc.) into an existing display.

According to various embodiments, SSVEP can be generated up to 90 Hz and the flicker fusion rate is around 40 Hz. Thus various examples incorporate a frequency range that allows for the stimulation and consequent generation of SSVEPs even though the user perceives a steady light in a respective display. Although the highest SSVEP amplitudes are generated in the 6 Hz-16 Hz band (i.e., low frequency band), these flicker rates are perceptible, annoying, and disrupt any display in which they are introduced. Even though conventional approaches suggest using the low frequency band to obtain strong signals, the inventors have realized unique and novel advantages in higher frequency bands. For example, the system enables unobtrusive stimuli and identifies options for resolving lower amplitude SSVEP using resulting from the use of higher frequency signals, for example, based on longer detection times.

To provide an example, where an existing display of a virtual scene includes a chair, the chair itself is modified to flicker at a frequency in excess of the critical fusion rate. From the conscious perspective of the viewer of the virtual scene, nothing has changed in the display. Yet the system can detect SSVEP responsive to the user's focus on the chair. In further example, a full screen display can be partitioned into several of these stimulating elements, which will be integrated as part of the virtual scene. Again the user does not consciously perceive any difference in the display.

According to various embodiments, the system is configured to execute different flickering frequencies, patterns, and/or harmonics to distinguish respective visual elements, and each visual element can encode object IDs and/or executable functions. The inventors have realized that even though multiple stimuli (e.g., visual elements) fall within the visual field of the user, only the one that receives the attention focus of the subject will elicit the corresponding SSVEP response in the user's brain.

According to one embodiment, the system enables a BCI that permits a user to navigate between application menus by looking at the interactive objects and respective menus options without conscious awareness of the flickering objects includes in the display. In another examples a menu of movie options is displayed with each visualization of a movie option flickering with a respective frequency and/or pattern. Responsive to looking at one of the options, for example, for a period of time, the system identifies the visual element being focused on based on associated SSVEP and maps the focused on visual element to a computer operation (e.g., choosing the movie to watch). From the perspective of the user, the user simply looks at an item on the screen and the computer executes the selection.

In some embodiments, the system can include visual indicators that are shown to the users as selections are being made. In some examples, to inform the user of target activation (e.g., selection, or execution, among other options), real-time feedback in the form of one or more loading bars is incorporated under each selectable object.

In various experimental implementation, users reported a satisfactory overall experience with subliminal interfaces, in part due to the unexpected responsiveness of the system, as well as due to the fact that virtual objects flickered at a rate that did not cause annoyance. Since the imperceptible visual stimuli can be integrated unobtrusively into any element of the virtual world, the applications of the system reach various situations where knowing user's visual focus can be relevant to executing any computer function.

Figure 3:
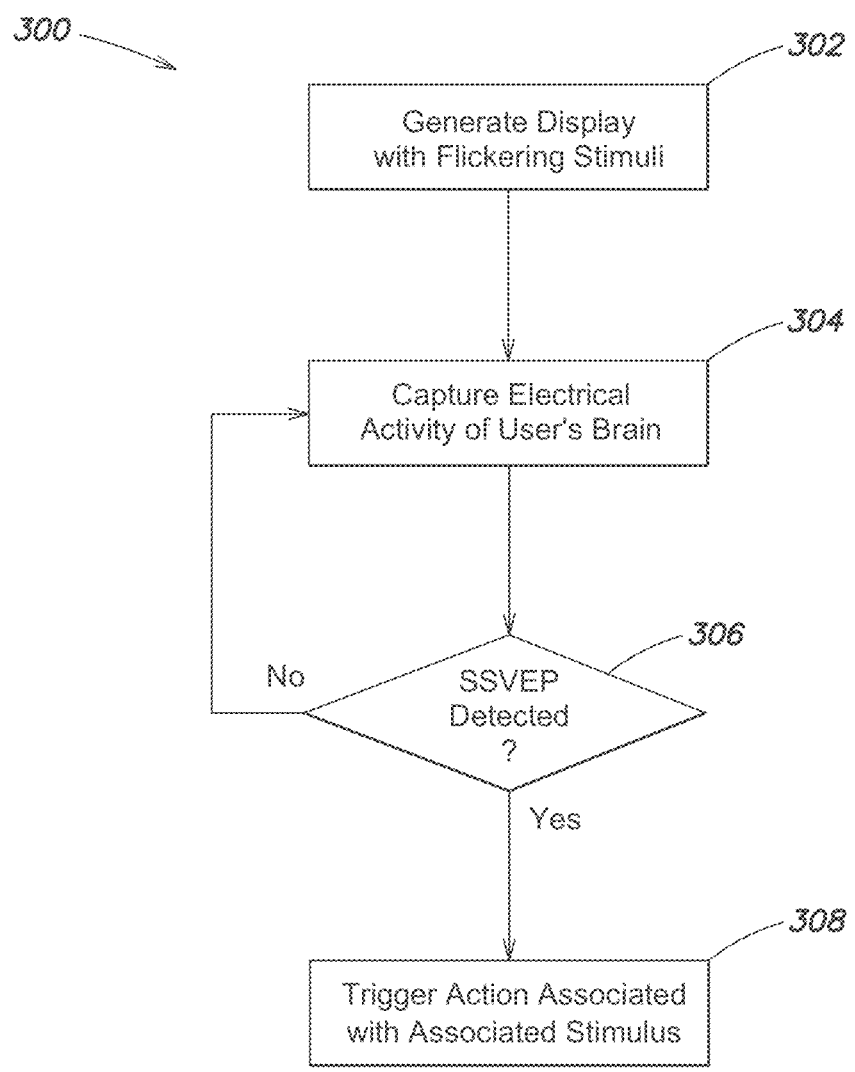
FIG. 3 is an example process flow for triggering computer operations based on visual selection of consciously imperceptible flickering stimuli, according to one embodiment.
Figure 4:
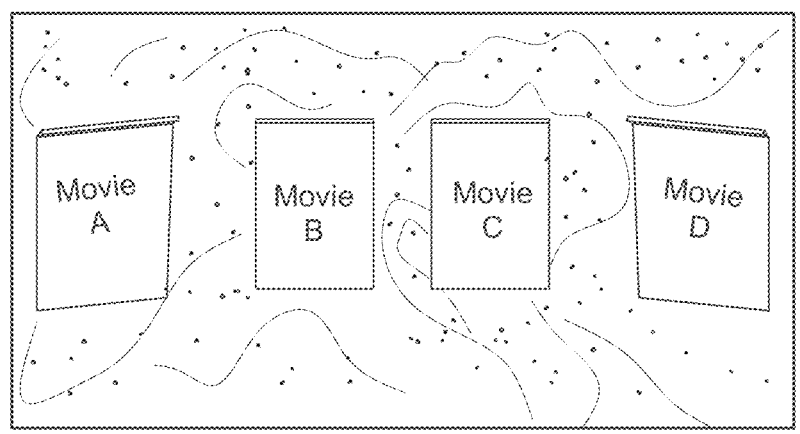
FIG. 4 is a visually selectable menu display, according to one embodiment.

FIG. 3 illustrates an example process flow 300 for triggering computer operations based on visual selection of consciously imperceptible flickering stimuli. Process 300 beings with generation of a display that includes flickering stimuli at 302. The flickering stimuli are generated so that the frequency of the flickering occurs at a rate greater than the critical fusion rate. In various examples, the critical fusion rate can be different based on the properties of the display, color, luminance, positioning within the display, etc. In some system and process embodiments, different minimum flicker rates for different visual elements can be set to ensure that the flickering stimuli are not perceived by the user. For example, visual elements shown in the periphery of display can be generated with higher frequencies as peripheral vision is more sensitive to flickering stimuli. In further embodiments, flickering frequencies can be dynamically changed, for example, as a peripheral visual element moves into the user's central visual field.

Process 300 continues with capture of electrical activity of the user's brain at 304. For example, EEG sensors are integrated into a VR headset or other headgear to capture brain activity. The capture data is analyzed at 306 to determine if a visual stimulus is evoking a steady state potential in the user's brain. As discussed above, responsive to a user focusing on a flickering stimulus, an SSVEP is produced that is associated with the frequency, pattern, and/or harmonics of the flickering stimulus.

If an SSVEP is detected 306 YES, an action associated with the respective stimulus is executed at 308. For example, if the visual element having the flicker frequency associated with the SSVEP in the display is a menu option, the associated action is a selection operation associated with the menu. In various embodiments, based on execution of process 300 any computer input operation can be translated into a visual selection and execution of the associated input. If no SSVEP is detected, process 300 continues with capture of brain activity (e.g., 304) and further analysis of the data to determine if SSVEP are produced (e.g., 306).

Example Display Device and Example Augmented Function

According to various aspects, a display with a high refresh rate is used to permit creation and display of visual elements having a high flicker frequency (e.g., having a refresh rate of at least 80 Hz). In one example, the known Oculus Rift® VR headset was used to render the display—as the system is configured to render stimuli above the flicker fusion rate, it was determined that the Rift's refresh rate (RR) of 90 Hz was sufficient and enables generation of stimulating signals at frequencies up to 45 Hz (i.e. half the RR).

The inventors have also realized that stimuli signals generated by the system (e.g., a VR display) are constrained by respective refresh rate (RR) of the associated display, since rendered images can only be updated once every 1/RR seconds (1/90 for the Oculus Rift®). Therefore, an 'on/off' stimulation pattern (max/min screen luminance respectively) could only generate sub-multiples of the refresh rate. It was realized that using max/min as an approach (with a 90 Hz RR), stimuli signal frequencies would quickly drop below the flicker fusion rate, which is undesired. According to other embodiments, given displays with a higher RR, this consideration becomes less meaningful, and in some examples, max/min signals can be used given a sufficient RR.

In various experimental executions, the system was configured to implement a sampled sinusoidal stimulation method which allows the system to execute stimuli signals at any frequency up to half of the refresh rate. For example, such signals can be generated by modulating the luminance $L(f_{st}, k)$ of the display screen using the following expression:

$$L(f_{st}, k) = 0.5 \sin(2\pi f_{st}(k/RR)) + 0.5 \quad (1)$$

where $f_{st}$ is the flickering frequency of the visual stimulus, k is an integer that indicates the frame index in the sequence and RR corresponds to the refresh rate of the display. $L(f_{st}, k)$ represents a sampled sine of frequency $f_{st}$ with a sampling rate of RR Hz. The dynamic range of the signal is from 0 to 1, where 0 represents dark and 1 maximum luminance.

Since all stimuli frequencies are set higher than the flicker fusion rate and lower than half of the refresh rate, and considering the flicker fusion rate to be 40 Hz, the targeted frequency band for this implementation was 40 Hz-45 Hz.

Beating Effect and Remediation Examples

Figure 2A:
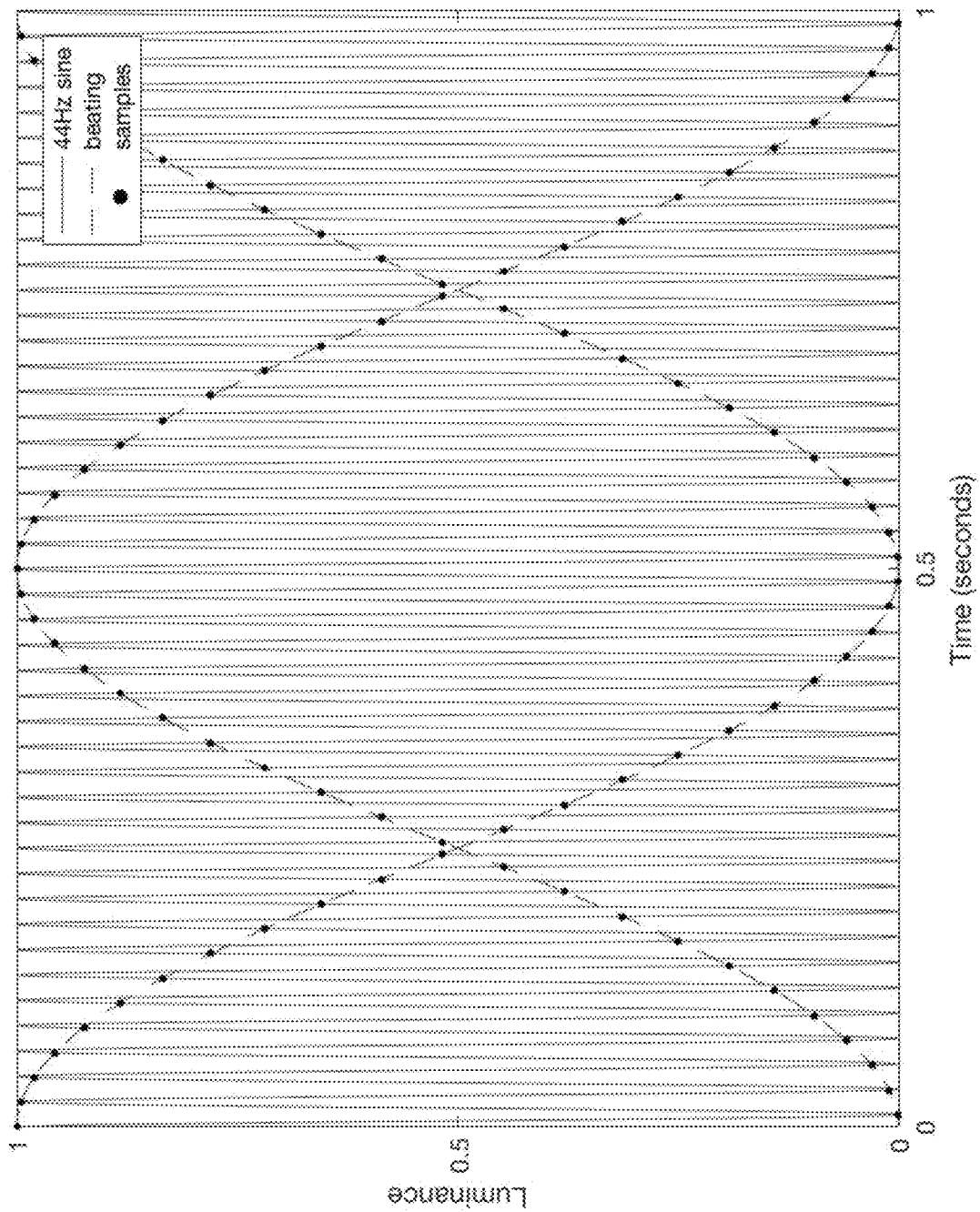
FIG. 2A is graph showing an apparent beating effect induced on an example display.

The inventors have further realized that the sampling a wave of a frequency very close to the Nyquist rate can cause the emergence of apparent beats in a display. These beats oscillate at a frequency $f_{beat}$:

$$f_{beat} = 2(F_s/2 - f_{st}) \quad (2)$$

where $F_s$ is the sampling frequency and $f_{st}$ is the frequency of the sampled signal. Since in this example, the system operates with $F_s$=90 Hz, the apparent beats generated oscillate at $f_{beat}$=90−2$f_{st}$. An example of the apparent beating effect for a 44 Hz sine is shown in FIG. 2A where the background illustrates a 44 Hz stimulating sine wave sampled at RR=1/90 Hz (black dots representing samples). The dashed line shows the beating effect that will be perceived. This sampling effect translates into an undesired perception of a slowly ($f_{beat}$) oscillating luminance. Various embodiments are configured to minimize or eliminate this effect. In one example, a stimulating sine signal with lower amplitude is used on the system to eliminate this effect. Other embodiments can utilize screens with higher refresh rates to eliminate this effect. For displays that are susceptible, reducing the stimulating sine signal can resolve this issue.

$$L_2(f_{st}, k) = 0.3 \sin(2\pi f_{st}(k/RR)) + 0.7 \quad (3)$$

In this example, the luminance $L(f_{st}, k)$ is modulated as a sine wave with an amplitude of 0.3, so the signal produced ranges from 0.4 to 1. The smaller ranges generate smaller amplitude beats, and the fading effect is barely perceptible by any user. However, the inventors have realized that the beating effect disappears at the expense of power reduction of the stimulus and consequently of the SSVEPs. Reducing power in some examples requires longer SSVEP measurement times. As a consequence, various embodiments provide different levels of power reduction balanced against different levels of perceptible beating effects. For example, without reducing the signal amplitude, the beating effect will be perceivable as long as $f_{beat} \leq f_{fusion}$. Solving for the refresh rate of the display and assuming $f_{fusion}$=40 Hz leads to RR$\leq$2$f_{st}$+40 Hz. Therefore, the minimum refresh rate that will allow for maximized amplitudes of the visual stimuli while preserving their non-perceptiveness is given by:

$$RR_{min} \geq 2f_{st} + 40 \text{ Hz} \quad (4)$$

The Oculus Rift® VR headset currently available was used in an example execution and has a refresh rate of 90 Hz, which does not fulfill Equation 4 for stimulating frequencies $f_{st}$ higher than $f_{fusion}$. Thus in this example, the system was configured with amplitude reduction of the stimuli signal to prevent the user from noticing the beating effect. The amplitude reduction affects corresponding SSVEP amplitudes, which in turn argues for the use of higher refresh rate displays (for example, in other embodiments) to avoid the need for balancing (e.g., lower power and/or longer detection times balanced against perceptible beating effect).

Figure 2B:
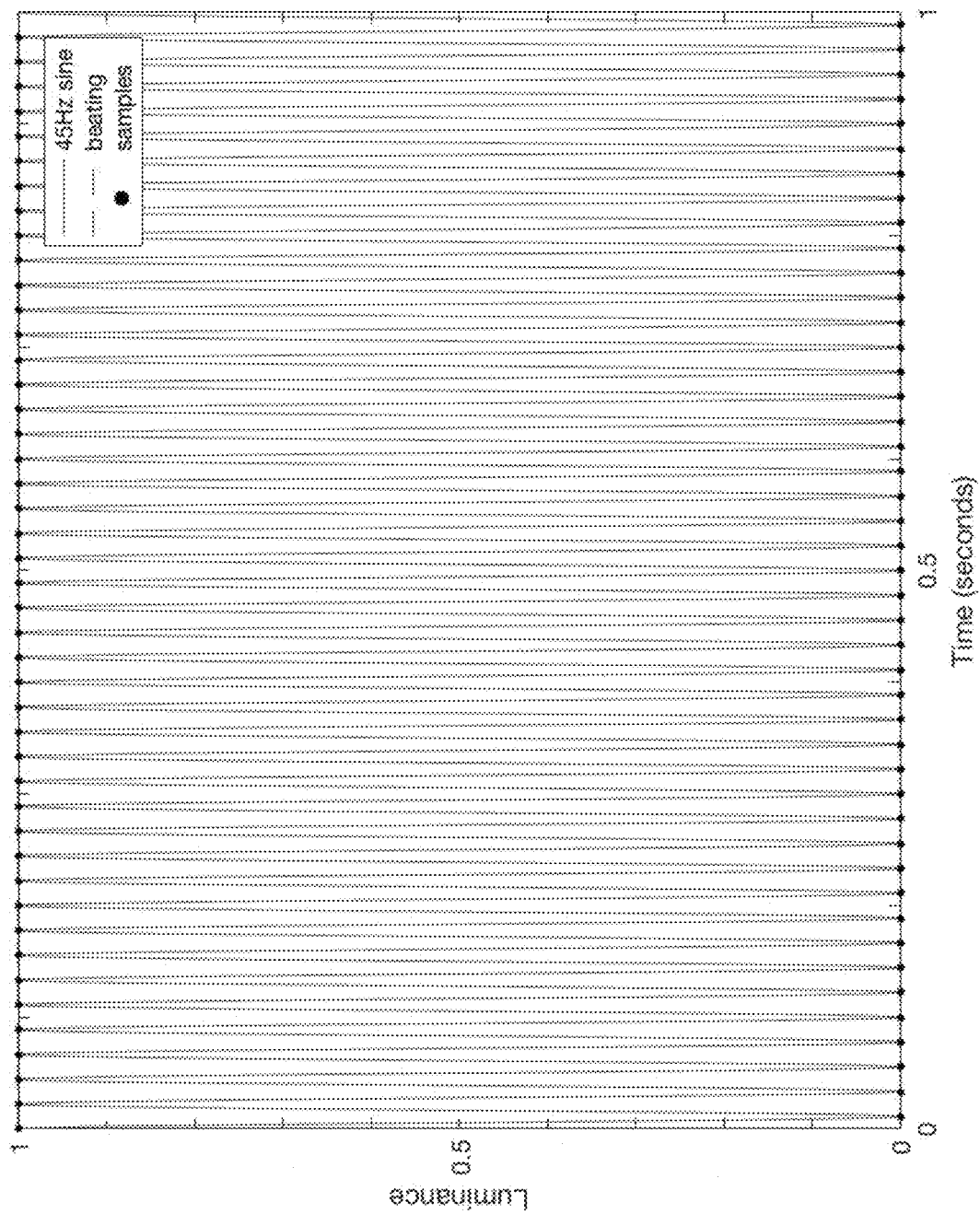
FIG. 2B is graph showing resolution of the beating effect, according to one embodiment.

According to one example, a particular result occurs when the stimulating frequency equals half the refresh rate. In this example, using Equation 2 above it is observed that when the stimulating frequency equals half the refresh rate, $f_{beat}$=0 Hz, which indicates that there will not be a beating effect. As is shown in FIG. 2B, no beating wave is created and sampled frames happen to fall at the maximum and minimum values of the 45 Hz sine wave, which corresponds to maximum and minimum luminance values respectively. Therefore, an on/off sequence (square wave) is created under these parameters; and since its frequency is still above the flicker fusion rate, such visual elements remain imperceptible. In this example, there is no need to modify the luminance function $L(f_{st}, k)$. Other embodiments can be tuned to various RR of specific displays or devices. And in further embodiments, displays or devices with high enough RR can be used such that beating effects are eliminated without any amplitude adjustments.

Example Virtual Reality Application

According to one embodiment, a virtual environment was developed using Unity3D® and augmented to include visual elements with consciously imperceptible visual stimuli. In one example, the environment includes two different type of scenes. The first/starting screen is a main menu display with four different movie covers shown on the screen. The user can select from the displayed movie options based on focusing on a particular movie. According to one embodiment, each movie cover has a different stimulating signal associated, with frequencies $f_{st}=\{42, 43, 44, 45\}$ Hz. As discussed above, the system is configured to capture SSVEPs produced when the user focuses on one of the visual elements having the respective flickering frequency. Thus, the user can pick the movie to watch by just gazing at the desired cover without the need of any joystick or hand controller. The corresponding SSVEP signals generated are detected by the EEG electrodes and the detected SSVEP signal mapped to the computer function where the application executes a transition to play the selected movie and/or move playback scene.

According to one embodiment, the second screen type is configured to show a display playing the movie the user selected in the main menu. In some examples, displayed in the bottom-left corner (for an example placement) of the screen there is displayed a selectable visual object to allow the user to navigate back to the main menu. The visual object is also an integrated visual stimulus (e.g., visual element) with its associated frequency (e.g., $f_{st}=42$ Hz) and the user may look at it to trigger the system to stop the movie and switch to the display to the starting menu.

Example Real-Time Feedback Objects

According to some embodiments, the system is configured to display selection indicators to inform the users that the system is detecting a selection and will operate responsive to their intentions. In one example, the system generates real-time feedback in the form of loading bar displays below each selectable object (see FIG. 5). When the system detects the user is gazing at an object, the corresponding bar starts loading, and it takes a period of time to (e.g., 4 seconds) to fully charge and trigger the system to execute an associated action (e.g., begin the transition to the selected scene). In the case the user stops gazing at the loading object, the system is configured to reset the bar automatically and any associated action is suspended. Various execution thresholds can be used to prevent false selection and the threshold tuned to the specific environment in which they are used. For example, in a gaming context/environment a short period of time facilitates a faster and more responsive gaming experience (threshold may be 0.1, 0.2, 0.5, 1, 2, 3, 4, seconds or any other option substantially within or around that range). In the static menu example above, shorter or longer selection times can also be used.

Example EEG Recording Equipment

Various embodiments integrate EEG electrodes directly into VR headsets or headbands worn by a user. In the Oculus Rift® example, the headsets have a triangle-shaped back strap that cradles the back of the head and is equipped with part of the headset tracking system. This shape and position of the strap is adapted to carry three EEG electrodes in positions Pz, O1 and O2 according to the known international 10-20 system. In this embodiment, reference and ground electrodes were placed in the ear lobes with ear clips. As for the EEG recording equipment, the system can be configured with Bluetooth® low energy data transmission, which provides a sampling rate of 200 Hz. Other embodiments can use different data transition modalities and different sampling rates.

Example SSVEP Detection

According to various embodiments, the system (e.g., 100, engine 102 and/or detection component 106) can be configured to analyze data from the EEG sensors using a number of methods. In one example, the system is configured to execute a canonical correlation analysis in order to detect elicited brain signals. In canonical correlation analysis (CCA): given two variable sets X, Y and their linear combinations:

$$x = XW_x^T, \ y = YW_y^T$$

CCA finds the weight vectors $W_x$ and $W_y$, which maximize the correlation p between x and y by solving the following:

$$\max_{W_x, W_y} \rho = \frac{E[W_x X^T Y W_y^T]}{\sqrt{E[W_x X^T X W_x^T] E[W_y Y^T Y W_y^T]}} \qquad (5)$$

In this example, define $X \in R L \times N$ as the recorded EEG data, where L and N denote the number of samples of the EEG signal and the number of EEG channels respectively. With three electrodes (N=3) the matrix X takes the form:

$$X = [X1 X2 X3] \qquad (6)$$

where $X_i \in R^{L \times 1}$. In another example, define $Y_f \in R^{L \times 2H}$ as the artificially generated sinusoidal signals of frequency f and its multiples used as the reference, where H represents the number of harmonics. In this example, the duration of the signals X and $Y_f$ are the same. Each submatrix of $Y_f$ contains the pair cos ($2\pi hf\ t$) and sin($2\pi hf\ t$), where h=1, 2, ... H. The amplitude of the SSVEP (fundamental h=1 and harmonics h>1) resulting from high stimulation frequencies (>40 Hz) is considerably lower than in low-frequency SSVEP. Thus, analysis can be constrained to the fundamental frequency H=1 for the reference signals $Y_f$, giving:

$$Y_f = [\cos(2\pi ft) \sin(2\pi ft)] \qquad (7)$$

Applying CCA to X and $Y_f$, the correlation will be maximized by enhancing the part of the evoked response (present in $Y_f$), and by reducing the noise (not present in $Y_f$), thereby improving the signal-to-noise ratio of the filtered signal x. With four possible stimulation frequencies ($f_{st}$ {42, 43, 44, 45} Hz), the system defines four different reference signal matrices $Y_f$: Y42, Y43, Y44, Y45. Then, the system determines a correlation value pf for each pair $Y_f$, X and identify the targeted frequency as the one that gives a higher pf. For every data segment, the system can determine a correlation vector $$R \in \mathbb{R}_{\geq 0}^{1 \times 4}:$$

$$R = [\rho 42 \ \rho 43 \ \rho 44 \ \rho 45] \qquad (8)$$

which contains the four correlation values resulting from applying CCA (e.g., four times).

Further analysis can be configured to discriminate whether an elicited SSVEP is present in the captured EEG signals. In one embodiment, the system uses the condition as the maximum $\rho f_{max}$ needs to fulfill with respect to the other three $\rho f$. According to one example, empirical determination can be avoided by using logistic regression as a simple binary classification model. In the binary classification approach, the model takes as input the following features derived from the correlation vector R:

$$S = \sqrt{\frac{\sum_{f=1}^{4}(\rho_f - \mu_R)^2}{3}} \quad (9)$$

Difference between maximum correlation $\rho_{fmax}$ and the second highest one.

Difference between maximum correlation $\rho_{fmax}$ and sum of the other three With these features as input, the binary model outputs a positive or negative answer. If positive, our system considers the recorded EEG signal contains the elicited SSVEP and the targeted frequency will be the one corresponding to the maximum correlation $\rho_{fmax}$. In the case of a negative response, the analysis determines that the EEG data is empty of SSVEP and the user is not currently looking at an stimulus.

Real Time Data Processing Example

According to one embodiment, the system is configured to process EEG signals in 5 seconds time windows (in other examples shorter and longer time windows may be used), with 4 seconds of overlap so that the system updates every second. In further embodiments, each window (e.g., 5-second slice) of raw EEG is first band-pass filtered with a finite impulse response filter (e.g., of order 10) and cutoff frequencies (e.g., 10 Hz and 50 Hz). Once filtered, CCA is applied to the filtered data segment and each reference signal matrix $Y_f$, with which the vector of correlations R are determined. A trained logistic regression classification model is then applied to the features computed from R and a system output is given.

According to various embodiments, the system can also be configured to prioritize minimizing false positives since they can be annoying for users in such an application where the human-computer communication happens in the "background". Thus, according to some implementations, the system state (e.g., execution of an associated computer operation) is not changed until two equal consecutive outputs are given by the SSVEP detection algorithms. In other embodiments, execution can be triggers upon a first detection. The various embodiments can be tuned dynamically, and for example, based on confidence levels of SSVEP detection.

Experimental Prototype

Figure 5:
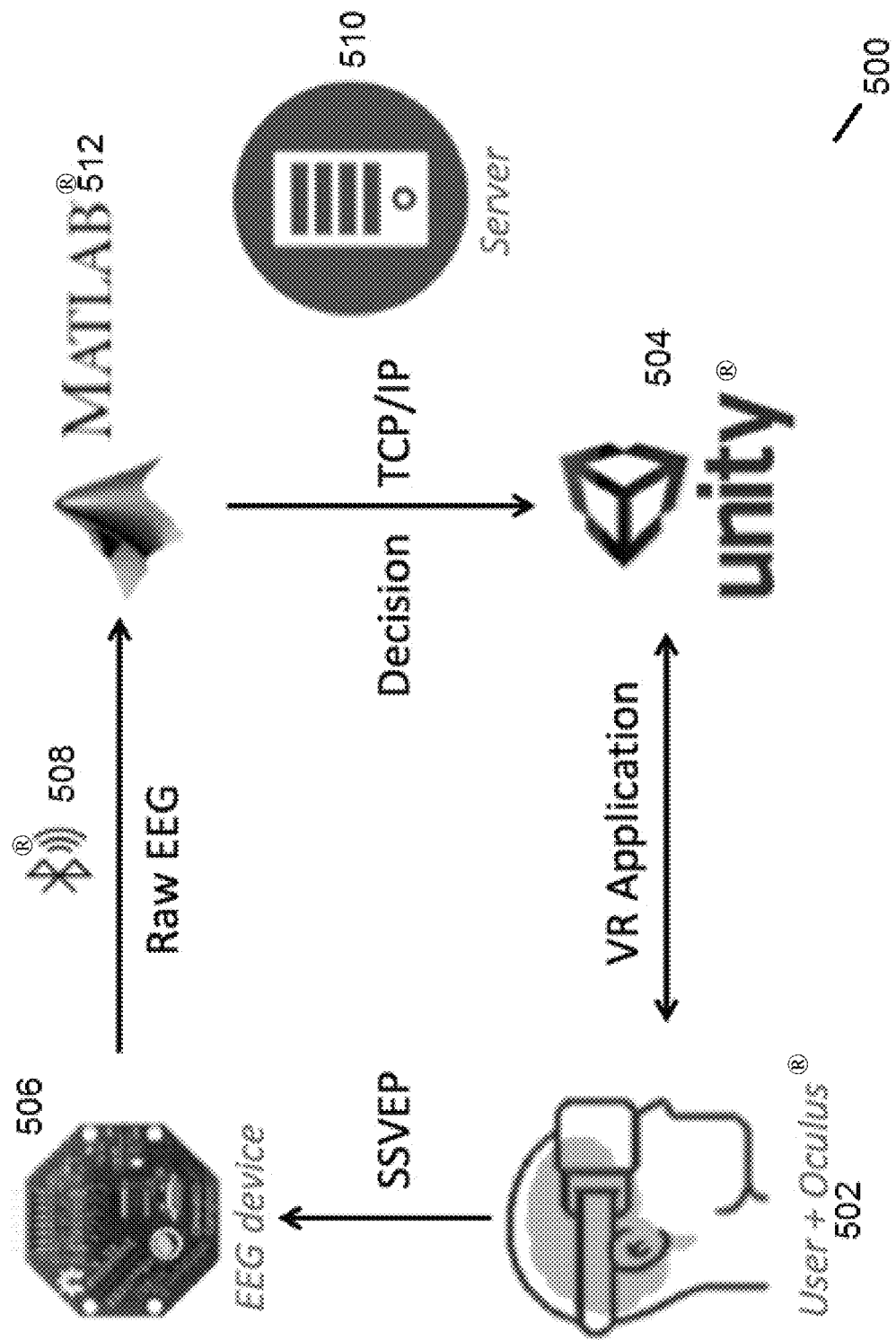
FIG. 5 is a block diagram of system components and communication pathways, according to one embodiment.

FIG. 5 is a block diagram 500 of elements used in a prototype implementation. A VR headset was used to display visual elements in a virtual scene (e.g., 502 Oculus Rift® VR headset). The headset is connected to a computer running a VR application (e.g., 504 Unity3D® application). In the prototype, EEG data is captured by sensors embedded in the VR headset (e.g., recorded at 506 by OpenBCI's Ganglion board). The data can be transmitted through Bluetooth® Low Energy (BLE) (e.g., at 508) to a server (e.g., 510) running a processing environment (e.g., Matlab® 512). In this prototype, the Matlab® code is programmed to process EEG signals perform and SSVEP detection in real time. In this prototype, Matlab® is connected to the Unity3D® application via TCP/IP and communicates updated information when applicable.

Experiments were conducted using the prototype and volunteer users. In the experiments, conductive electrode paste was used to improve the EEG signal acquisition, and electrode impedance was always kept below 20 kOhms. Setup time for each user was about 5 minutes, which comprised accommodating VR headset to subject, adjusting electrodes to obtain good connection and launching the system online. During the experimental execution, an external computer display showed the view of the user so that the researcher managing the experiment could follow the tasks performed by the subject and properly time each experiment. The average length of the sessions was about 45 minutes.

Figure 6:
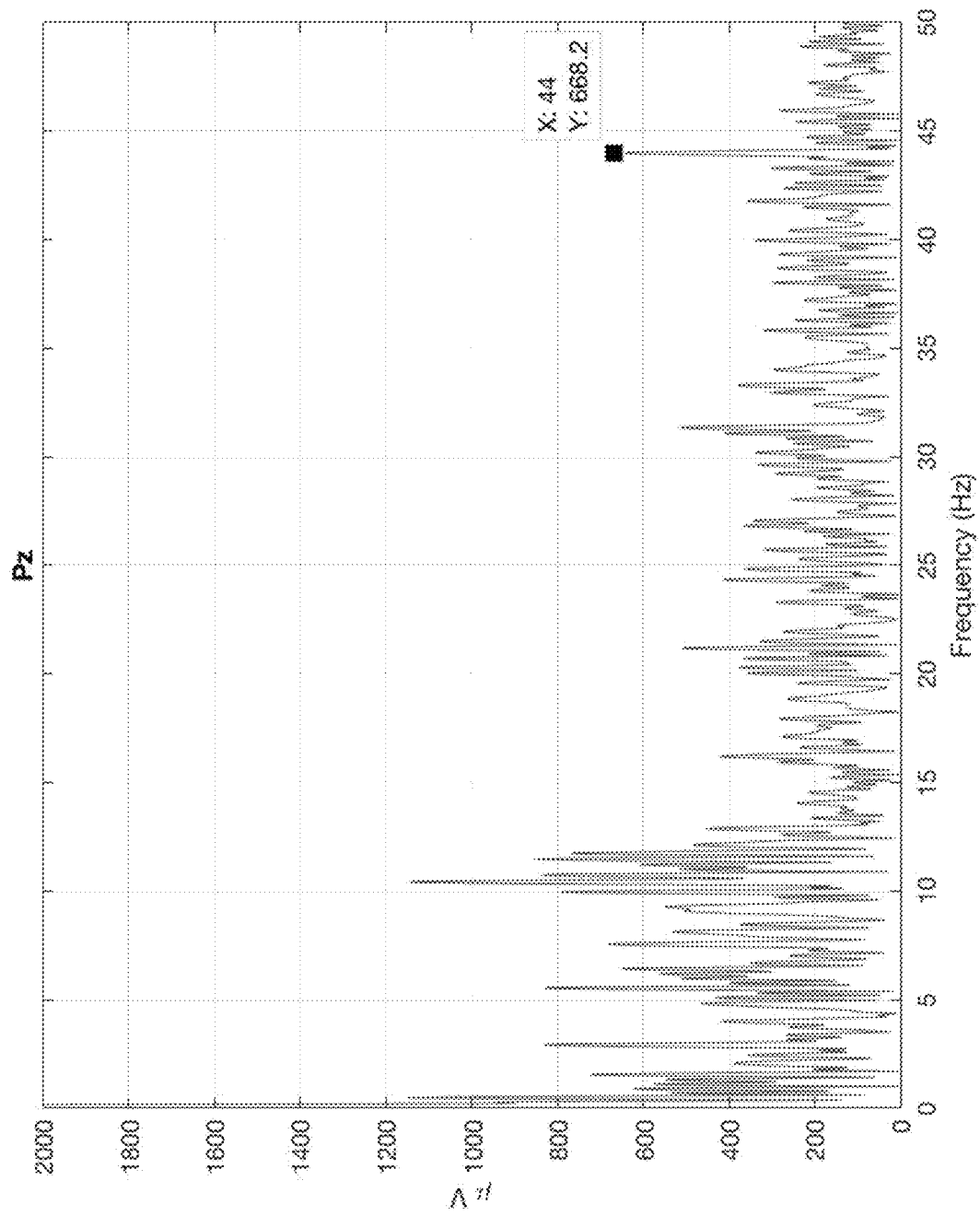
FIG. 6 is a graph of an example SSVEP, according to one embodiment.

FIG. 6 is a fast fourier transform (FFT) plot of a 5 second window of unfiltered EEG dates corresponding to the Pz location. In this example, the user was focusing on a visual element having a flickering frequency of 44 Hz.

Trainer Augmentation Example

As discussed above, the system uses flickering stimuli where the flickering is not consciously detectable. With flicker frequencies above the critical fusion rate, these stimuli do not appear to flicker at all and have no perceptible effect on a given display. In many scenarios the critical flicker fusion rate for a user can vary. Various embodiments can implement frequencies at rates above an estimated critical fusion rate to compensate. In other embodiments, the system can include a trainer application configured to detect a critical fusion rate for a given user and/or for respective applications and displays. Further, the trainer application can be used to establish flicker frequencies that a given user identifies as perceivable, and thresholds beyond which the user can no longer perceive the flicker. In various embodiments, the trainer can generate various flickering stimuli having different flicker frequencies and request user feedback on perceptible versus imperceptible. The system can train on various frequencies, positions in the display, color, luminance, etc. The trained data points can provide baseline information to modify visual elements introduced into displays, so that regardless of position, color, luminance, etc. the introduced visual elements remain consciously imperceptible. In other embodiments, trainer applications can be executed separately from BCI system to establish various baselines or set floor frequencies at which all or most users will not consciously perceive a flickering stimulus.

According to one example, the system can start with a frequency in a margin above an estimated critical fusion rate, and incrementally reduce the frequency until respective visual elements are perceivable. This approach can be executed with visual elements in various positions on the display screen to establish tailored critical fusion rates, and further can be executed for various colors and/or color combinations to refine applicable critical fusion rates. In some embodiments, the system can use the information captured by the trainer application to set minimum flicker rates for various visual elements.

Figure 8:
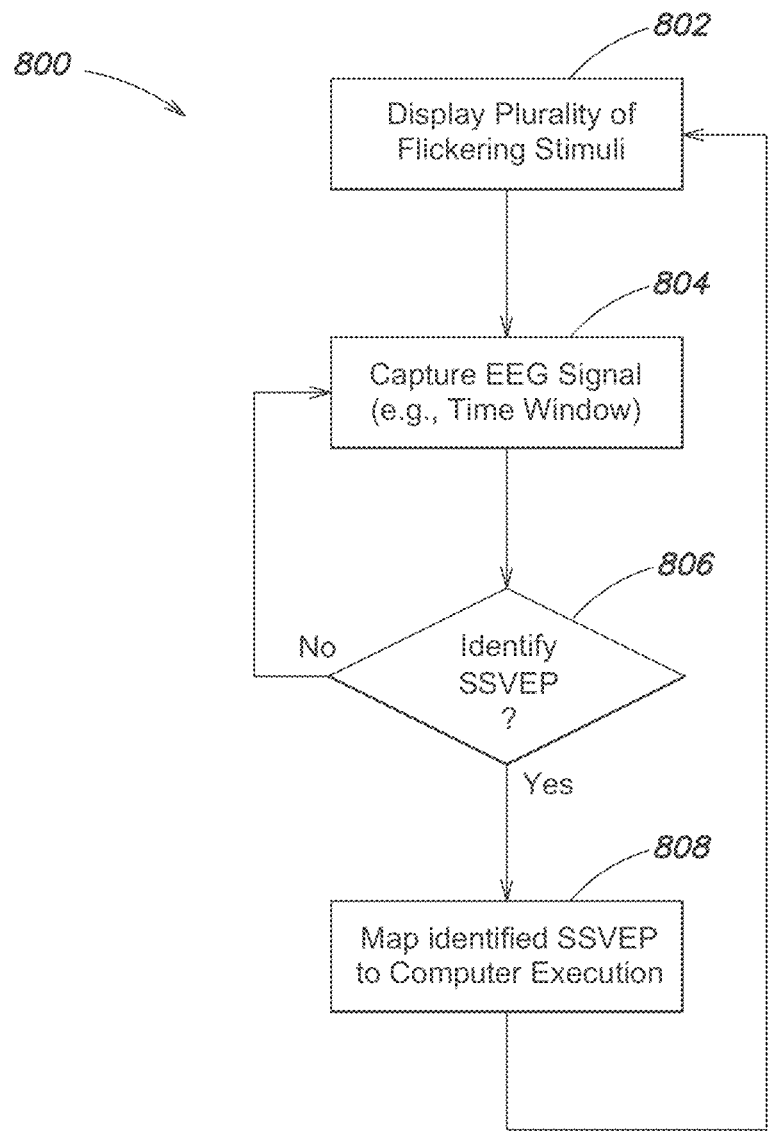
FIG. 8 is an example process flow for detecting SSVEP, according to one embodiment.

FIG. 8 shows an example process 800 that can be executed with any running process and associated displays to detect a variety of SSVEP, and trigger various computer operations associated with the various SSVEP. Process 800 begins with display of a plurality of flickering stimuli as part of a content display at 802. While the user is viewing the content display, process 800 continues with capture of EEG signals at 804, which can be done for set intervals or time windows. In one embodiment, the process 800 is configured to capture/process overlapping time windows (e.g., 4, 5, 6, seconds) with an offset (e.g. 1, 1.5, 2 second offset) so data is processed at the offset period. At 806, process 800 identifies within the processed brain activity SSVEP (806YES) or continues to capture/process brain activity at 804 if no SSVEP is detected (806NO).

Identifying SSVEP can include determining which visual element having a unique flicker rate is being focused on by the user (e.g., at 806YES) by identifying an associated evoked potential in the user's brain activity. In one example, flicker rates of 42 Hz, 43 Hz, and 44 Hz can be used with three visual elements shown simultaneously. Identification of the respective potentials (e.g., at 806), allows the execution of 800 to determine which visual element is being focused on by the user.

In various embodiments, each visual element can be associated with different computer operations (e.g., animate a display of the user moving right, animate a display of the user moving left, up, down, etc.). In further embodiments, computer operations can include a mapping to a native program selection operation (e.g., in a program developed without BCI functionality). In one example, the computer operation translates user focus on a visual element into a mouse click or other selection of the visual element—passing the selection operation to the underlying program. At 808, the identified SSVEP can be mapped to the respective computer operations, and those operations can be executed in response. In various embodiments, process 800 can be executed continuously while an application is running that used embodiments of the BCI.

It should be appreciated that various examples above each describe functions that can be and have been incorporated in different system embodiments together. The examples and described functions are not exclusive and can be used together.

Figure 7:
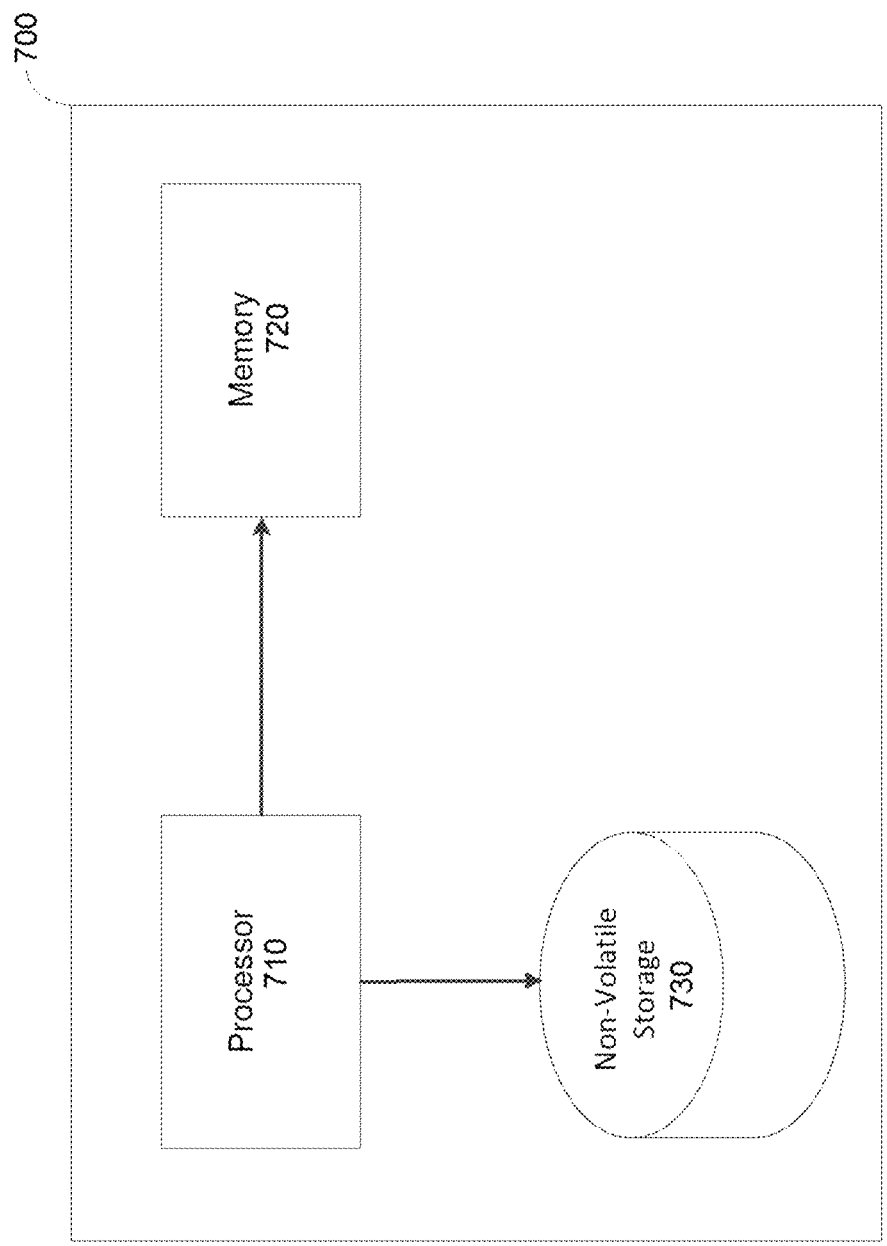
FIG. 7 is a block diagram of a special purpose computer system programmed to execute various ones of the functions disclosed herein.

Modifications and variations of the discussed embodiments will be apparent to those of ordinary skill in the art and all such modifications and variations are included within the scope of the appended claims. An illustrative implementation of a computer system 700 that may be used in connection with any of the embodiments of the disclosure provided herein is shown in FIG. 7. The computer system 700 may include one or more processors 710 and one or more articles of manufacture that comprise non-transitory computer-readable storage media (e.g., memory 720 and one or more non-volatile storage media 730). The processor 710 may control writing data to and reading data from the memory 720 and the non-volatile storage device 730 in any suitable manner. To perform any of the functionality described herein, the processor 710 may execute one or more processor-executable instructions stored in one or more non-transitory computer-readable storage media (e.g., the memory 720), which may serve as non-transitory computer-readable storage media storing processor-executable instructions for execution by the processor 710.

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples (e.g., the processes described with reference to FIG. 3, the various system components, analysis algorithms, processing algorithms, etc.) have been provided. The acts performed as part of each process may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, and/or ordinary meanings of the defined terms. As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

The invention claimed is:

1. A system for controlling a brain computer interface, the system comprising:
    at least one processor operatively connected to a memory;
    a stimulus generator, executed by the at least one processor, configured to generate visual elements for rendering in a display showing content without change perceptible to a viewing user, wherein the stimulus generator is further configured to modulate luminance of at least one visual element in the display at a frequency exceeding a critical fusion rate to display the at least one visual element with an associated flicker rate executed at the frequency exceeding the critical fusion rate to the viewing user;
    at least one electroencephalogram (EEG) sensor to capture brain activity of the viewing user observing the display including the at least one visual element; and
    wherein the at least one processor is configured to:
        determine the display viewed by the user is subject to an induced visual effect that would result from rendering the at least one visual element, based on a refresh rate associated with the display;
        eliminate the induced visual effect, wherein elimination of the induced visual effect includes an operation to tune an amplitude of a stimulating signal associated with the at least one visual element to the refresh rate associated with the display;
        detect a visually evoked potential in the captured brain activity of the viewing user associated with the at least one visual element that is induced by modulation of the luminance of the at least one visual element; and
        trigger at least one computer function mapped to the respective at least one visual element based on the visually evoked potential detected that is associated with the at least one visual element.

2. The system of claim 1, wherein the stimulus generator is configured to modify an existing display of content to incorporate the visual elements.

3. The system of claim 2, wherein the stimulus generator is configured to modify the existing display without change perceptible to a viewing user relative to the unmodified display.

4. The system of claim 1, wherein the at least one processor is configured to generate the at least one visual element and associated modulated luminance with amplitude reduction relative to a maximum/minimum stimulation pattern.

5. The system of claim 1, wherein respective visual elements concurrently observable in a display are associated with respective unique modulation frequency or modulation pattern to evoke a respective steady-state visually evoked potential ("SSVEP").

6. The system of claim 5, wherein the respective visual elements are associated with respective unique SSVEP based on the respective unique modulation frequency or modulation pattern.

7. The system of claim 5, wherein the at least one processor is configured to identify a presence of the respective SSVEP in the brain activity captured from the at least one EEG sensor.

8. The system of claim 5, wherein the stimulus generator is configured to generate a plurality of visual elements with the respective unique modulation frequency or modulation pattern, and wherein the respective unique modulation frequency or modulation pattern includes at least one of unique frequency, unique stimulation pattern, unique stimulation timing, or unique stimulation encoding.

9. The system of claim 1, wherein the at least one processor is further configured to process time intervals of EEG data at partially overlapping time periods.

10. A method for controlling a brain computer interface, the method comprising:
    generating, by at least one processor, visual elements for rendering in a display showing content without change perceptible to a viewing user, wherein generating the visual elements includes modulating luminance of at least one visual element in the display at a frequency exceeding a critical fusion rate to display the at least one visual element having an associated flicker rate at a frequency exceeding a critical fusion rate to the viewing user;
    determining, by the at least one processor, that the display viewed by the viewing user is subject to an induced visual effect that would result from flickering the at least one visual elements based on a refresh rate associated with the display;
    eliminating, by the at least one processor, the induced visual effect, wherein eliminating of the induced visual effect includes tuning an amplitude of a stimulating signal associated with the at least one visual element to the refresh rate associated with the display;
    capturing, by the at least one processor, brain activity of the viewing user observing the display including the at least one visual element from at least one electroencephalogram (EEG) sensor;
    detecting, by the at least one processor, a visually evoked potential in the brain activity associated with the at least one visual element that is induced by modulation of the luminance of the at least one visual element; and
    triggering, by the at least one processor, at least one computer function mapped to the respective visual element based on the visually evoked potential detected that is associated with the at least one visual element.

11. The method of claim 10, wherein the method further comprises an act of modifying, by the at least one processor, an existing display of content to incorporate the visual elements.

12. The method of claim 11, wherein the act of modifying the existing display is executed without change perceptible to a viewing user relative to the unmodified display.

13. The method of claim 10, wherein the method further comprises generating, by the at least one processor, the at least one visual element and associated modulated luminance with amplitude reduction relative to a maximum/minimum stimulation pattern.

14. The method of claim 10, wherein the method further comprises associating, by that at least one processor, respective visual elements concurrently observable in a display with respective unique modulation frequency or modulation pattern to evoke a respective steady-state visually evoked potential ("SSVEP").

15. The method of claim 14, wherein the method further comprises associating, by that at least one processor, the respective visual elements are associated with respective unique SSVEP based on the respective unique modulation frequency or modulation pattern.

16. The method of claim 14, wherein the method further comprises, identifying, by the at least one processor, a presence of the respective SSVEP in the brain activity captured from the at least one EEG sensor.

17. The method of claim 14, wherein method further comprises generating respective visual elements with at least one of: a unique frequency, a unique stimulation pattern, a unique stimulation timing, or a unique stimulation encoding.

18. The method of claim 10, wherein the at least one processor is further configured to process time intervals of EEG data at partially overlapping time periods.

19. A non-transitory computer-readable medium having computer readable instructions when executed cause a computer to execute a method for controlling a brain computer interface, the method comprising:

generating visual elements for rendering in a display showing content without change perceptible to a viewing user, wherein generating the visual elements includes modulating luminance of at least one visual element in the display at a frequency exceeding a critical fusion rate to display the at least one visual element having an associated flicker rate at a frequency exceeding a critical fusion rate to the viewing user;

determining that the display viewed by the viewing user is subject to an induced visual effect that would result from flickering the at least one visual element, based on a refresh rate associated with the display;

eliminating the induced visual effect, wherein eliminating of the induced visual effect includes tuning an amplitude of a stimulating signal associated with the at least one visual element to the refresh rate associated with the display;

capturing brain activity of the viewing user observing the display including the at least one visual element from at least one electroencephalogram (EEG) sensor;

detecting a visually evoked potential in the captured brain activity associated with the at least one visual element that is induced by modulation of the luminance of the at least one visual element; and triggering at least one computer function mapped to the respective visual element based on the visually evoked potential detected that is associated with the at least one visual element.

20. The non-transitory computer-readable medium of claim 19, wherein the method further comprises an act of modifying, by at least one processor, an existing display of content to incorporate the visual elements without change perceptible to a viewing user relative to the unmodified display.

* * * * *

UNITED STATES PATENT AND TRADEMARK OFFICE
CERTIFICATE OF CORRECTION

PATENT NO. : 11,445,972 B2
APPLICATION NO. : 16/379096
DATED : September 20, 2022
INVENTOR(S) : Sanjay E. Sarma et al.

It is certified that error appears in the above-identified patent and that said Letters Patent is hereby corrected as shown below:

In the Claims

In Claim 10, at Column 18, Line 45:
"least one visual elements based on a refresh rate"
Should read:
--least one visual element, based on a refresh rate--

Signed and Sealed this
Fourteenth Day of February, 2023

Katherine Kelly Vidal
*Director of the United States Patent and Trademark Office*